United States Patent [19]

Yozwiak

[11] Patent Number: 5,244,385
[45] Date of Patent: Sep. 14, 1993

[54] DENTAL MIXING SLAB AND METHOD OF USE

[76] Inventor: Raymond A. Yozwiak, 2040 Bridgeport Dr., Lexington, Ky. 40502

[21] Appl. No.: 744,529

[22] Filed: Aug. 13, 1991

[51] Int. Cl.⁵ ............................................. A61C 1/14
[52] U.S. Cl. ........................................ 433/49; 433/77
[58] Field of Search ............... 433/49, 77; 219/392, 219/443; 269/302.1; 206/63.5

[56] References Cited

U.S. PATENT DOCUMENTS

| | | | |
|---|---|---|---|
| 434,737 | 8/1890 | Teal | 433/49 |
| 1,137,482 | 4/1915 | Hanly | 433/49 |
| 1,247,406 | 11/1917 | Jefferies | 433/49 |
| 1,278,153 | 9/1918 | Jefferies | 433/49 |
| 1,539,428 | 5/1925 | Romaine | 433/49 |
| 1,660,493 | 2/1928 | Proctor | 76/107.1 |
| 1,896,772 | 2/1933 | Drespel | 433/49 |
| 1,980,533 | 11/1934 | Kile | 433/49 |
| 1,982,155 | 11/1934 | Earman | 433/49 |
| 1,993,450 | 3/1935 | Lowry | 433/49 |
| 3,858,410 | 1/1975 | Drake | 433/77 |
| 3,890,096 | 6/1975 | Nichol et al. | 206/63.5 |
| 3,922,879 | 12/1975 | Arnold | 433/77 |
| 4,948,368 | 8/1990 | Kanotscher | 433/77 |

*Primary Examiner*—John J. Wilson
*Attorney, Agent, or Firm*—Laurence R. Letson

[57] ABSTRACT

A dental mixing slab is described as having a heat sink and depending support members to space the heat sink from a supporting surface such as a counter or table. The dental mixing slab is formed out of stainless steel which is highly thermal conductive and is not damaged by heating and cooling. Heating is required to sterilize the mixing slab to avoid the transmission of disease from patient to patient or between patient and dental worker. Heating will not damage the dental mixing slab.

3 Claims, 1 Drawing Sheet

DENTAL MIXING SLAB AND METHOD OF USE

FIELD OF THE INVENTION

The invention relates to the field of dental instruments, tools and devices and more specifically to the slabs upon which cements, medicants and the like are mixed, particularly those slabs that may be sterilized using heat or heat in combination with steam or chemicals.

BACKGROUND OF THE INVENTION

Some diseases may be communicated by the transmission of body fluids between infected and uninfected individuals or contact with infected materials. Prevention of such infection depends upon breaking the chain of transmission.

In the practice of dentistry and related professions, procedures such as root canals, installing crown and bridge work, implanting inlays, cementing orthodontic appliances and other procedures which require movement of a tool from the patient's mouth to the mixing slab to acquire mixed cement or medicants, create the opportunity for the contamination of the mixing slab with any infection of the patient. While some infections are short-lived and pose no significant health risk, others are persistent and are not readily killed by disinfection procedures.

Present practices in a dental or related practice follow either a disinfection or a sterilization approach. In the chemical disinfection approach, the implements used to treat one patient are washed and then disinfected with a suitable disinfectant, such as glutaraldehyde or glutaraldehyde oxide, by soaking the tools and implements in the disinfectant for an extended period of time. If the soaking of the tools and implements is prolonged for a sufficiently long period, for example, six to ten hours, the disinfectant soaking is tantamount to sterilization.

The alternative to the chemical disinfectant soak is sterilization with heat, heat and steam, or heat and chemicals. Sterilizing with heat, with or without steam or chemicals, is much more rapid and permits the tools and implements to be reused more frequently. This reduces the number of sets of tools necessary to establish a dental or orthodontic practice, particularly when the practice has several work stations and where multiple patients are served simultaneously.

Typically, an autoclave is used to heat the washed dental tools and implements to an elevated temperature and to hold that temperature for a short time in comparison to the time for soaking disinfection.

The autoclave heats the contents rapidly to a temperature of about 250-275 degrees F. (121-134 degrees C.) for a period of 15-40 minutes, then the contents are allowed to dry. With dry heat, the tools are maintained at about 320 degrees F. (160 degrees C.) for two hours. In a Chemclave the conditions for sterilization are to maintain the objects as 270 degrees F. (132 degrees C.) for twenty minutes.

Glass plate dental mixing slabs are presently very widely used in most practices and are the only reusable slabs available from most dental supply houses. When these glass slabs are heated in an autoclave, dry heat oven or Chemclave, the exterior of the slab is heated much more rapidly than the interior of the typically ¼ to ⅜ inch thick slab of glass. The rapid heating of the slab creates internal stresses in the glass mixing slab and the slab may crack or shatter.

Similarly, if the slab survives the heating portion of the cycle, the rate at which glass cools is much slower than the rate of the steel of which the other items used in the practice are fabrocated and, therefore, the glass mixing slab is still very hot when the autoclave cycle is complete. When the door of the autoclave is opened, the ambient air of the room will replace the air of the autoclave and the thermal shock of the cool air may cause the slab to crack or shatter, as the exterior glass attempts to contract more rapidly than the interior portions.

Accordingly, the use of glass slabs requires that a dental office have large numbers of the slabs available and use long term soaking to sterilize the slabs, or alternatively, the use of an oven or autoclave which has a very long, slow heat up and cool-down cycle to prevent damage to the glass mixing slab. This also necessitates a separate heating device for the slabs, or the other tools would not be available for repeated use as rapidly as possible.

Further the cements and adhesives used to attach crowns, bridges, inlays, orthodontic appliances or other items to the teeth, often are materials that create an exothermic reaction when mixed. The cement and adhesive materials are also of a heat-sensitive nature, setting faster in a warm environment and slower in a colder environment.

When the cement is mixed, it is desired to keep the temperature of the mix at a temperature well below the set temperature allowing the item to be cemented, worked, placed appropriately, and positioned in place. Allowing the mix to overly warm during either the mixing or the time when it is resident on the slab prior to its use, will result in set-up before it can be used, necessitating mixing another batch of cement.

Pot life, the time the cement may be worked and used, may be extended by cooling. With glass slabs, this cooling is accomplished by refrigerating the slab prior to use. The mass of the glass slab is sufficient to act as a substantial heat sink to draw the exothermically produced heat from the mix and maintain the cement mix below the set temperature. When a glass slab is sterilized by heat, the slab must be cooled to approximately room temperature before the slab can be transferred to a refrigerator; otherwise, the slab will crack in the cold air of a refrigerator.

Some dental supply houses sell plastic mixing slabs. When the plastic slabs are heated, they will tend to soften and potentially become misshapen. Further the plastic material is much more likely to be cut, scratched or deformed in use, creating sites for contamination and residual cement to be trapped.

With a higher emphasis on sterilization of dental implements, it is less practical to use glass or plastic mixing slabs in a sterile dental office environment. To only disinfect the slab defeats the sterilization of the remainder of the tools and implements that come in contact with the glass slab.

U.S. Pat. No. 1,993,450 to Lowry, describes a thin plate of chrome/nickel alloy which is supported by a wood base. The mixing plate may be cleaned and sterilized but the wood base may not be heat sterilized readily, since the repeated heating and cooling of the wood would cause the wood to unduly dry and crack and be unserviceable.

U.S. Pat. No. 1,980,533 suggests the benefits of cooling, but uses a porous ceramic material to hold water for evaporative cooling of the ceramic slab and, thence, the cement mix. This approach is afflicted with the same short comings as a glass slab, since the glazed surface is essentially similar to glass. Further the porous nature of the device provides crevices and openings in which contaminants may reside. If evaporative cooling is used, then sterile water or alcohol must be used.

U.S. Pat. No. 1,137,482 to Hanly suggests an approach to sterile environments, but with no heat sinking capability, multiple cement mixes are required for an extended procedure, or the pot life of the cement is very limited.

U.S. Pat. Nos. 434,737 to Teal and 1,278,153 to Jefferies both disclose glass mixing slabs of varying configurations.

U.S. Pat. No. 1,660,493 to Proctor discloses a pallet of a somewhat similar shape. The Proctor pallet is described as usable for the manufacture of bricks, blocks and the like. The pallet is described as having exceptionally sharp edges and the process described by Proctor is adapted to produce such sharp edges. Sharp edges would be a hazard to the dentist or dental assistant and would open the possibility of cuts, from which the infection may be transmitted or the infection from the patient may be acquired by the dental worker through such cuts. In addition the inside corner of a sharp edged slab would be difficult to clean and thus difficult or impossible to sterilize adequately.

SUMMARY OF THE INVENTION

A dental mixing slab fabricated of a stainless steel will serve the needs of a mixing surface. The stainless steel mixing slab of the present invention also addresses the needs of the dental practice, by supporting the mixing surface at a height above the support table or counter that is comfortable for the dentist or assistant.

The connection between the slab working surface and the support legs is a gentle radius which allows easy interior surface cleaning and safety for the dental assistant or the dentist.

The supporting legs of the mixing slab are formed by bending the stainless steel plate downward to form a shallow inverted "U" shaped channel. The legs also space the top or work surface away from the counter or table so that the top or work surface is not significantly warmed by contact with the support surface.

The mixing slab is fabricated of stainless steel plate thick enough to provide a substantial heat sink for the exothermically produced heat of the cement.

An object of the invention is to provide the ability to heat sterilize a dental mixing slab.

Another object of the invention is to provide cooling to the cement being mixed.

A further object of the invention is to provide dissipation of the heat generated by the cement mix.

An additional object of the invention is to raise the mixing surface of the body of the mixing slab a sufficient distance to enable the dental assistant or dentist to comfortably mix the cement.

The problems and shortcomings of the prior art are overcome and the objects of the invention accomplished by this invention, a better understanding of which may be gained from the drawing and the detailed description to follow.

DETAILED DESCRIPTION OF THE BEST MODE FOR CARRYING OUT THE INVENTION

Figure 1:
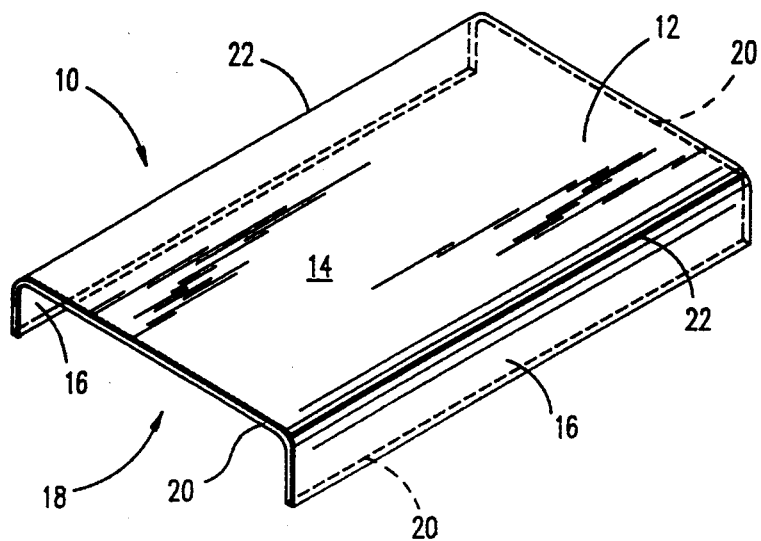
FIG. 1 is an elevated perspective view of the sterilizable dental mixing slab.

Referring to FIG. 1, the sterilizable dental mixing slab 10 is illustrated with a top or working surface 12. The working surface may be of any convenient size but is typically about six inches long and three inches wide.

The working surface 12 is a surface of a body 14 of stainless steel or other rust and corrosion resistant metal. The body is preferably about ⅛ inches (3.175 mm) in thickness. While a thinner section of material may be substantial enough to withstand the working forces of mixing the cement, the mass of the thinner material may not provide the ability to absorb as much heat as is necessary to extend the pot life of the cement mix.

The mixing slab 10 is preferably fabricated of stainless steel plate of 11 gauge which has a nominal thickness of 0.125 inches (3.175 mm).

To space the work surface 12 of the mixing slab from a support such as a table or counter, supporting members 16 depending from the body 14 are provided. The preferred method of fabrication is to bend the support members 16 to approximately perpendicular to the body 14. Typically the height of the support members is chosen to permit the comfortable mixing of cement on surface 12 using a spatula. Approximately ⅞ inch (22.2 mm) of height is comfortable for most users.

The channel 18 formed by the body 14 and support members 16 provides atmospheric insulation between the table or counter and the body 14. Any heat conducted to the body 14 through support members 16 will have to pass through a small cross section of the stainless steel in contact with the table or counter.

The region of junction between the support members 16 and body 14 is a gentle curved region 18. The gentle curvature of the curved region 18 is desirable to avoid injury to the user as the hand moves a spatula over the surface 12, mixing the cement. If the fingers or knuckles of the user contact the slab, they will not be cut or the user's gloves will not be torn or pierced.

The exposed edges 20 of the mixing slab 10 are free of sharp edges and burrs for the same reason that the region 18 is curved and smooth.

The preferred finish for the working surface 12 is a smooth mill finish. A polished or mirror finish is not essential. The mill finish is sufficiently free of surface imperfections to prevent the trapping or accumulations of cement residue in surface irregularities and thus retaining contaminants, while providing sufficient resistance to enhance the mixing of the cement.

The body 14 of the mixing slab 10 is a mass of stainless steel which, when cooled, is sufficient to absorb the heat generated by the exothermic reaction of the components of the dental cement. The larger the mass of the body 14, the greater the heat absorption capability. However, it is desired not to make the slab 10 unduly heavy as then it will take longer to heat and cool in an autoclave, during the sterilization cycle.

Figure 2:
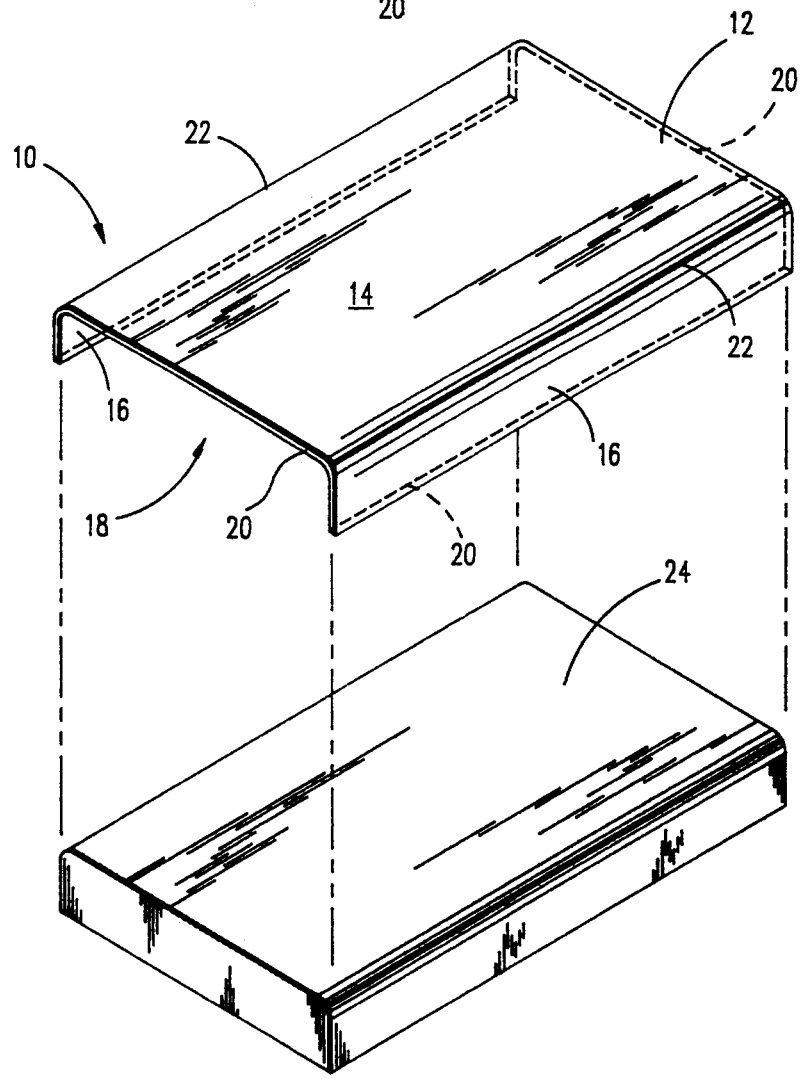
FIG. 2 is an elevated perspective view of the sterilizable dental mixing slab with a mating supplemental heat sink.

Should it be desirable to increase the heat sink capacity of the dental mixing slab 10 above that possessed by the mixing slab 10, an additional heat sink capacity may be added. The addition of the heat sink is shown in FIG. 2. A refrigerated block 24 of stainless steel or similar material is positioned under the mixing slab 10 and in contact with the underside of the body 14. The cold temperature or chill of the block 24 will act to cool the mixing slab 10 by conducting heat absorbed by the mixing slab 10 away from the mixing slab 10 and into the block 24. The block 24 may also be sterilized between uses as is the mixing slab 10. The block 24 will be substantially heavier and less easily handled than the mixing slab 10 and would accordingly be used only in a lengthy procedure to avoid repeated mixing of cement batches.

The slab 10 may be cooled to a very low temperature if desired. The slab 10 my be placed in a freezer or refrigerator even when still hot or warm from the autoclave or sterilizing device. The thermal shock to the material is not harmful to the slab 10. The internal stresses within the stainless steel dissipate rapidly due to the ability of the steel to conduct heat from the center to the surface where it is absorbed by the air in the refrigerator.

The steps of use of the slab 10 for mixing dental cement are: providing the slab 10 as illustrated in FIG. 1, heating the slab 10 to sterilize the mixing slab 10, using one of the processes described above; freezing the slab 10 to reduce its temperature, placing the cement components on the working surface 12 and mixing the components. The working surface cools the cement mixture by absorption of the exothermic heat generated by the reaction of the dental cement mixture.

The ability of the mixing slab 10 to cool the cement as it is mixed and as it resides on the working surface 12 may be increased when the procedure using the cement takes longer than the slab is capable of acting as a heat sink. The slab could be re-cooled by carbon dioxide or other compressed, non-toxic gas from a highly pressurized container blown on the under side of the body 14. As the gas expands, it becomes supercooled by expansion; and when it contacts the body 14 of mixing slab 10, will cool the body 14, thereby, restoring the capacity of the body 14 to continue cooling the cement mix. This recooling of the body 14 is efficient due to thermal conductivity of the stainless steel as compared to the thermal conductivity of glass. Further, the glass mixing slab could crack or shatter due to rapid cooling of the exterior of a glass mixing slab.

The smooth mill finish on the slab 10 and particularly the working surface 12, is smooth enough to permit the slab to be wiped and washed for normal cleaning prior to sterilization. Sterilization is not a substitute for cleaning and washing the mixing slab, since the residue of the mixed cement must be removed prior to the next usage.

The gentle curved region 22 joining of the support members 16 to the body 14 of the mixing slab 10 is advantageous where cleaning of the slab 10 is concerned. The exterior and interior surfaces of the corners 22 may be wiped clean with a wipe cloth, tissue or scrubbed with an abrasive scrubber similar to those used to scrub pans in a kitchen. With curvature rather than a sharp edge on the exterior, injury is avoided. With the smooth curved interior surface of corner 22, any material which may have migrated from the working surface 12 may be easily removed by wiping or scrubbing, and there is no need to resort to other implements to remove the material from small inaccessible crevices.

The dental mixing slab 10, being made of stainless steel, may be placed in an autoclave, Chemclave or dry heat oven, with other dental tools and implements for sterilization. The sterilization devices heat the air in the chamber to an elevated temperature as rapidly as the heating elements can elevate the temperature. The metal composition is not adversely affected by the rapid heating. The thermal shock to the dental mixing slab 10 from the hot atmosphere of the autoclave will have no ascertainable effect on the slab. Unlike the glass slabs which will shatter or crack, the stainless steel mixing slab 10 will withstand the rapid heating and cooling and not be damaged.

While the best mode of carrying out the preferred embodiment of the invention has been shown and described, it should be understood that changes to the invention may occur to one of skill in the art and may be made in the invention without departing from the scope of the invention as defined in the claims.

I claim:

1. A dental mixing slab comprising:
    a body;
    said body having a work surface, said work surface comprising a smooth, uninterrupted and unobstructed surface upon which dental cement may be mixed;
    supporting members formed from said body as flanges bent to a position depending from said work surface and forming a region at which said support members join said body;
    said region at which said support members join said body comprising a smooth bend having a radius at least two times the thickness of the material from which said body and said supporting members are made,
    said slab fabricated from a oxidation resistant metal alloy; and
    said body comprising a heat sink,
    whereby said work surface is supported spaced from a surface and where said body cools dental cement mistures to delay the normal heat setting of said cement mixtures.

2. A method of preparing dental cement comprising:
    providing a heat sink of a highly heat conductive metal;
    providing a stainless steel mixing surface on said heat sink,
    providing support means for maintaining said heat sink and said mixing surface spaced from a supporting surface;
    heating said heat sink, support means and said working surface to a temperature of at least above the boiling temperature of water for a period of time exceeding the minimum time required to render said mixing surface sterile;
    cooling said heat sink and said surface to a temperature below the freezing point of water;
    placing on said working surface components of said cement to be mixed; and
    mixing of said components thoroughly; and
    cooling said mixture by maintaining said mixture in cooling contact with said working surface.

3. The method of mixing dental cement of claim 2 further comprising:
    providing a secondary heat sink of a metal having a high heat conductivity;
    cooling said secondary heat sink to a temperature below the freezing point of water;
    mating said secondary heat sink in surface to surface relation to said heat sink having said working surface, whereby heat absorption capacity of said secondary heat sink cools said other heat sink and said working surface thereby extending the functional cooling capability of said working surface.

* * * * *